United States Patent [19]

Picard et al.

[11] Patent Number: 5,510,100
[45] Date of Patent: Apr. 23, 1996

[54] OIL-IN-WATER EMULSIONS CONTAINING AN AUTO-EMULSIFIABLE COMPOSITION BASED ON A FATTY ALCOHOL AND ON AN ALKYL POLYOSIDE AND A CO-EMULSIFYING AGENT

[75] Inventors: Elisabeth Picard; Jacqueline Lambert, both of Paris; Jacqueline Griat, Ablon, all of France

[73] Assignee: L'Oreal, Paris, France

[21] Appl. No.: 258,025

[22] Filed: Jun. 10, 1994

[30] Foreign Application Priority Data

Jun. 10, 1993 [FR] France ................................. 93 07004

[51] Int. Cl.$^6$ ................................. A61K 7/42; A61K 7/40
[52] U.S. Cl. ........................... 424/59; 514/772; 514/777; 514/786; 514/788; 514/844; 514/937; 514/938
[58] Field of Search ..................................... 514/777, 772, 514/786, 788, 937, 938; 424/59

[56] References Cited

FOREIGN PATENT DOCUMENTS

| 0006741 | 1/1980 | European Pat. Off. . |
| 9115184 | 10/1991 | WIPO . |
| 9206778 | 4/1992 | WIPO . |

OTHER PUBLICATIONS

Amalric C. Michel–Lecocu Seppic & Proserqio "Cetearyl Glucoside: New Approach to Sun Care Emulsions" DCI Mar. 1994 pp. 40–44.

*Primary Examiner*—C. Warren Ivy
*Assistant Examiner*—Evelyn Huang
*Attorney, Agent, or Firm*—Cushman Darby & Cushman

[57] ABSTRACT

Cosmetic or dermatological composition in the form of a stable oil-in-water emulsion, characterized in that it contains:

(a) from 5 to 40% by weight of an oily phase which may contain, in a proportion of less than 15% by weight, at least one vegetable oil which has more than 40% by weight of linoleic acid triglycerides, (b) from 0.5 to 5% by weight of an auto-emulsifiable composition containing from 60 to 90% by weight of at least one fatty alcohol having from 12 to 22 carbon atoms, from 10 to 40% by weight of an alkyl polyoside, (c) from 0.5 to 4% by weight of at least one co-emulsifying agent chosen from fatty alcohols having from 14 to 22 carbon atoms, fatty acids having from 14 to 22 carbon atoms, alkyl glyceryl ethers, the alkyl chain of which has from 14 to 22 carbon atoms, the compounds of formula:

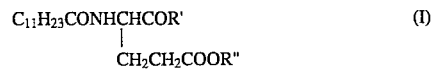

in which: R' and R", which may be identical or different, represent a cholesteryl, behenyl or 2-octyldodecyl radical, and the mixtures of the said co-emulsifying agents.

7 Claims, No Drawings

OIL-IN-WATER EMULSIONS CONTAINING AN AUTO-EMULSIFIABLE COMPOSITION BASED ON A FATTY ALCOHOL AND ON AN ALKYL POLYOSIDE AND A CO-EMULSIFYING AGENT

The subject of the present invention is a composition in the form of a stable, fine and homogeneous oil-in-water (O/W) emulsion which consists essentially of an oily phase which may contain, in a proportion of less than 15% by weight, at least one oil which has a high content of linoleic acid triglycerides, an auto-emulsifiable composition and a co-emulsifying agent, and its use in various cosmetic or dermatological applications.

It is known that the emulsions used in the cosmetic and dermatological fields generally contain, in order to facilitate their emulsification, surfactants of nonionic nature and of hydrophilic type, obtained by grafting a polyoxyethylated chain. For the purpose of avoiding the use of such surfactants, which are irritants to a greater or lesser extent on account of possible impurities due to their preparation processes, it has been proposed in application WO 92/06778 to use an auto-emulsifiable composition based on fatty alcohols and alkyl polyoside.

However, the emulsions obtained by the use of such an auto-emulsifiable composition are not totally satisfactory.

Indeed, they lack finesse and homogeneity and are particularly thick. In addition, when applied to the skin they penetrate it with difficulty, which makes them cosmetically fairly unacceptable.

It has now been surprisingly and unexpectedly observed that by combining a co-emulsifying agent, resulting from a very specific selection, with the auto-emulsifiable composition according to WO 92/06778, it was possible to overcome the abovementioned disadvantages.

The (O/W) emulsions according to the invention are indeed very stable, light and homogeneous, which corresponds with the criteria sought in cosmetics and in dermatology, particularly when the emulsions are intended for face or body care.

The subject of the present invention is thus a cosmetic or dermatological composition in the form of an oil-in-water emulsion containing:

(a) from 5 to 40% by weight of an oily phase which may contain, in a proportion of less than 15% by weight, at least one vegetable oil which has more than 40% by weight of linoleic acid triglycerides, (b) from 0.5 to 5% by weight of an auto-emulsifiable composition or combination containing from 60 to 90% by weight of at least one fatty alcohol having from 12 to 22 carbon atoms, from 10 to 40% by weight of an alkyl polyoside, the alkyl chain of which has from 12 to 22 carbon atoms and from 0 to 5% by weight of polyoside, (c) from 0.5 to 4% by weight of at least one co-emulsifying agent chosen from fatty alcohols having from 14 to 22 carbon atoms, fatty acids having from 14 to 22 carbon atoms, alkyl glyceryl ethers, the alkyl chain of which has from 14 to 22 carbon atoms, and the compounds of formula:

(I)

in which: R' and R", which may be identical or different, represent a cholesteryl, behenyl or 2-octyldodecyl radical, and the mixtures of the said co-emulsifying agents, with the proviso that when a lone co-emulsifying agent is present, its proportion by weight is equal to or less than 2%, the remainder essentially consisting of an aqueous phase.

According to a preferred embodiment, the weight ratio between the oily phase and the alkyl polyoside of the auto-emulsifiable combination is greater than or equal to approximately 15.

Among the oils of the oily phase there may be mentioned:

mineral oils such as paraffin oil, vaseline oil and mineral oils having a boiling point between 300° and 400° C.;

oils of animal origin such as perhydrosqualene;

oils of vegetable origin consisting of less than 40% by weight of linoleic acid triglycerides such as sweet almond oil, avocado oil, castor oil, olive oil, jojoba oil, groundnut oil, rapeseed oil, coconut oil, hazelnut oil, karite butter, palm oil, apricot seed oil and calophyllumoil;

synthetic oils such as purcellin oil, butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate, propylene glycol dicaprylate and esters derived from lanolic acid such as isopropyl lanolate, isocetyl lanolate and isoparaffins.

Among the oils which may be used according to the invention, there may also be mentioned: acetyl glycerides, the octanoates and decanoates of alcohols and of polyalcohols such as those of glycol and of glycerol, the ricinoleates of alcohols and of polyalcohols such as those of cetyl, fatty acid triglycerides such as caprylic/capric triglycerides, $C_{10}$–$C_{18}$ saturated fatty acid triglycerides, volatile or non-volatile silicone oils and fluorinated and perfluorinated oils.

Among the vegetable oils having more than 40% by weight of linoleic acid triglycerides there may be mentioned: corn germ oil, wheat germ oil, soybean oil, sunflower oil, sesame oil, grapeseed oil, evening primrose oil, safflower oil fatty acid, passion-flower oil and rye grain oil.

Among the auto-emulsifiable combinations or compositions described in WO 92/06778, there may in particular be mentioned the product marketed under the name "Montanov 68" by the company Seppic which essentially consists of the combination of approximately 77% of cetyl/stearyl alcohol ($C_{16}$–$C_{18}$) and approximately 23% of cetearyl glucosides.

According to a specific embodiment of the invention, the alkyl radical of the alkyl polyoside is identical to that of the fatty alcohol in the auto-emulsifiable composition.

According to a preferred embodiment of the compositions according to the invention, the weight ratio between the oily phase and the auto-emulsifiable composition is between 6 and 30.

Among the co-emulsifying agents which may be used in the compositions according to the invention, there may be mentioned among the fatty alcohols having from 14 to 22 carbon atoms, stearyl alcohol and cetyl alcohol and their mixtures, among the fatty acids having from 14 to 22 carbon atoms, stearic acid, and among the glyceryl alkyl ethers having an alkyl chain having from 14 to 22 carbon atoms, chimyl alcohol and batyl alcohol.

Among the compounds of formula (I) which may be used as co-emulsifying agents, there may be mentioned the product marketed under the name "ELDEW CL-301" by the company Ajinomoto.

As co-emulsifying agent belonging to the group of fatty acids having from 14 to 22 carbon atoms, a product of natural origin, namely sumac wax, which contains approximately 40% of $C_{16}$ fatty acids and 50% of $C_{18}$ fatty acids may be used according to the invention.

The compositions according to the invention may additionally contain various adjuvants. Among the adjuvants of the fatty phase there may in particular be mentioned dyes, lipophilic active principles, sunscreen agents, antioxidants and preservatives.

Among the adjuvants of the aqueous phase there may in particular be mentioned water-soluble derivatives such as dyes and preservatives, active principles such as sodium hyaluronate and magnesium gluconate, trace elements, biological derivatives such as urea, lactic acid, pyrrolidonecarboxylic acid and its salts, in particular its sodium salt, polyols such as propylene glycol, 1,3-butylene glycol, glycerol, polyglycerol, sorbitol, glucose and saccharose, salts such as magnesium sulphate and sodium chloride, clayey minerals which swell in aqueous medium such as saponite, hectorite and smectite, amino acids, aqueous gelling agents, for instance polysaccharides such as cellulose derivatives (carboxymethylcellulose, hydroxypropylmethyl cellulose, etc.), gums such as xanthan gum and carob gum, proteins such as sulphonic keratins, collagen and elastin, silicates such as aluminium silicate and magnesium silicate, acrylic derivatives such as Carbomers, glyceryl polyacrylates or polymethacrylates and polyacrylamides.

The compositions according to the invention may also contain various cosmetic ingredients such as essential oils, perfumes, pigments, fillers, vitamins and ceramides.

The compositions according to the invention, in the form of (O/W) emulsions, may be used in various cosmetic or dermatological applications, for example in the form of creams for the face, for the body, for the scalp or for the hair, or in the form of milks for the body or for removing make-up.

These compositions may also be used for make-up, in particular in the form of foundations, after the addition of pigments. They may also be used as sun creams after the addition of UV-B and/or UV-A filters or as after-sun creams or milks after addition of soothing compounds such as panthenol.

The (O/W) emulsions according to the invention are obtained according to the standard methods by hot mixing, at a temperature of approximately 70° C. of the fatty phase comprising the oily phase and the emulsifying agents and other additives to the aqueous phase with vigorous stirring followed by addition of the complementary amount of water and cooling.

Several examples of compositions according to the invention in the form of oil-in-water emulsions will now be given by way of illustration.

EXAMPLES OF COMPOSITIONS

EXAMPLE 1: Skin Care Cream

| | |
|---|---|
| Sesame oil | 10% |
| Hydrogenated polyisobutene | 15% |
| Auto-emulsifiable composition marketed under the name "Montanov 68" by the company Seppic | 3% |
| Stearyl alcohol | 2% |
| Stearic acid | 1% |
| Preservatives | 0.2% |
| Perfume | 0.1% |
| Sodium hydroxide | 0.012% |
| Glycerine | 3% |
| Water qs | 100% |

The cream obtained is stable, fine and homogeneous. It is smooth and penetrates well.

EXAMPLE 2: Skin Care Cream for Greasy Skin

| | |
|---|---|
| Cyclomethicone | 10% |
| Auto-emulsifiable composition marketed under the name "Montanov 68" by the company Seppic | 1.5% |
| Stearyl alcohol | 1% |
| Stearic acid | 0.5% |
| Preservatives | 0.2% |
| Sodium hydroxide | 0.006% |
| Xanthan gum | 0.2% |
| Propylene glycol | 3% |
| Water qs | 100% |

The cream obtained is light, smooth, feels fresh on application and penetrates well without feeling greasy on the skin.

EXAMPLE 3: Anti-ageing Fluid

| | |
|---|---|
| Apricot seed oil | 25% |
| Auto-emulsifiable composition marketed under the name "Montanov 68" by the company Seppic | 3% |
| Co-emulsifying agent marketed under the name "ELDEW CL-301" by the company Ajinomoto | 2% |
| Octyl methoxycinnamate | 1% |
| Mixture of titanium dioxide and aluminium stearate marketed under the name "Micro-titanium dioxide-MT 100T", by the company Tayca | 1% |
| Preservatives | 0.2% |
| Honey | 1% |
| Hydrolysed soybean protein | 0.1% |
| Glycerine | 3% |
| Water qs | 100% |

The cream obtained is fluid, very smooth and penetrates well. It has a good protecting effect.

EXAMPLE 4: Skin Care Cream

| | |
|---|---|
| Cyclomethicone | 10% |
| Mixture consisting of polyacrylamide/$C_{13}$–$C_{14}$ Laureth 7 isoparaffin | 0.8% |
| Auto-emulsifiable composition marketed under the name "Montanov 68" by the company Seppic | 2% |
| Stearyl alcohol | 1% |
| Stearic acid | 0.5% |
| Preservatives | 0.65% |
| Lysine | 0.025% |
| Ethylenediaminetetraacetic acid disodium salt | 0.05% |
| Xanthan gum | 0.2% |
| Glycerine | 3% |
| Water qs | 100% |

The cream obtained is fine, smooth and penetrates well.

EXAMPLE 5: Skin Care Cream

| | |
|---|---|
| Cyclomethicone | 10% |
| Mixture consisting of polyacrylamide/$C_{13}$–$C_{14}$ Laureth 7 isoparaffin | 0.8% |

-continued

| | |
|---|---|
| Perfluoropolymethylisopropyl ether | 0.5% |
| Auto-emulsifiable composition marketed under the name "Montanov 68" by the company Seppic | 2% |
| Stearyl alcohol | 1% |
| Stearic acid | 0.5% |
| Preservatives | 0.65% |
| Lysine | 0.025% |
| Ethylenediaminetetraacetic acid disodium salt | 0.05% |
| Xanthan gum | 0.2% |
| Glycerine | 3% |
| Water qs | 100% |

The cream obtained is stable, fine and homogeneous.

COMPARATIVE STUDY

A comparison was made, with regard to stability and finesse, between the (O/W) emulsion according to Example 2 above and the same (O/W) emulsion but containing no co-emulsifying agent, this emulsion having the following composition:

| | |
|---|---|
| Cyclomethicone | 10% |
| Auto-emulsifiable composition marketed under the name "Montanov 68" by the company Seppic | 1.5% |
| Preservatives | 0.2% |
| Sodium hydroxide | 0.006% |
| Xanthan gum | 0.2% |
| Propylene glycol | 3% |
| Water qs | 100% |

After the emulsions obtained had been left to stand for one hour at a temperature of 20° C., they were examined under a microscope at a magnification of 100.

Photos of the emulsions were then taken and these are attached under the references Photo (A) and Photo (B).

Photo (A) corresponds to the emulsion of Example 2 and Photo (B) to that of the Comparative Example.

As can be seen, the emulsion of Photo (A) is much finer and more homogeneous than that of Photo (B) which exhibits globules, indicating a lack of homogeneity and stability.

We claim:

1. A cosmetic or dermatological composition in the form of a stable oil-in-water emulsion, comprising
   (a) from 5 to 40% by weight of an oily phase optionally containing, in an amount less than 15% by weight, at least one vegetable oil containing more than 40% by weight of linoleic acid triglycerides,
   (b) from 0.5 to 5% by weight of an auto-emulsifiable composition containing from 60 to 90% by weight of at least one fatty alcohol having from 12 to 22 carbon atoms, from 10 to 40% by weight of an alkyl polyoside, the alkyl chain of which has from 12 to 22 carbon atoms,
   (c) from 0.5 to 4% by weight of at least one co-emulsifying agent selected from the group consisting of a fatty alcohol having from 14 to 22 carbon atoms, a fatty acid having from 14 to 22 carbon atoms, an alkyl glyceryl ether, the alkyl chain of which has from 14 to 22 carbon atoms, a compound of formula:

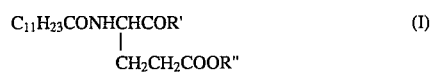

$$C_{11}H_{23}CONHCHCOR' \atop CH_2CH_2COOR''  \qquad (I)$$

wherein R' and R", each independently, represent a cholesteryl, behenyl or 2-octyldodecyl radical, and a mixture thereof, with the proviso that when a single co-emulsifying agent is present, said single co-emulsifying agent is present in an amount equal to or less than 2 weight percent, the remainder consisting essentially of an aqueous phase.

2. The composition of claim 1 wherein the weight ratio between said oily phase and said auto-emulsifiable composition is between 6 and 30.

3. The composition of claim 1 wherein said fatty alcohol of said auto-emulsifiable composition having from 12 to 22 carbon atoms is ($C_{16}$–$C_{18}$) cetyl/stearyl alcohol and said alkyl polyoside is cetearyl glucoside.

4. The composition of claim 1 wherein said co-emulsifying agent is selected from the group consisting of: stearyl alcohol, cetyl alcohol, stearic acid, chimyl alcohol, batyl alcohol and a mixture thereof.

5. The composition of claim 1 wherein said oily phase of the said oil-in-water emulsion also contains an adjuvant selected from the group consisting of a dye, a lipophilic active principle, a sunscreen agent, an antioxidant and a preservative.

6. The composition of claim 1 wherein said aqueous phase of said oil-in-water emulsion also contains an adjuvant selected from the group consisting of a dye, a preservative, a hydrophilic active principle, a trace element, a biological derivative, a polyol, a salt, a clayey mineral which swells in said aqueous phase, an amino acid and an aqueous gelling agent.

7. The composition of claim 1 which also contains at least one active substance selected from the group consisting of an essential oil, a perfume, a pigment, a filler, a vitamin, and a ceramide.

* * * * *